United States Patent [19]

Miller et al.

[11] Patent Number: 4,905,161

[45] Date of Patent: Feb. 27, 1990

[54] FLOW STABILITY REPORTING SYSTEM FOR A LIQUID CHROMATOGRAPHY SYSTEM

[75] Inventors: Les A. Miller, San Jose; Roberta Shafer, Milpitas, both of Calif.

[73] Assignee: Spectra-Physics, Inc., San Jose, Calif.

[21] Appl. No.: 142,581

[22] Filed: Jan. 11, 1988

[51] Int. Cl.$^4$ .................. G06G 7/57; G01N 31/00
[52] U.S. Cl. .................. 364/510; 364/502; 73/61/1 C; 210/101
[58] Field of Search ............ 364/497, 510, 500, 502, 364/509; 73/23.1, 61.1 C; 210/656, 101, 198.2, 741; 417/43, 20; 422/70

[56] References Cited

U.S. PATENT DOCUMENTS

| 4,128,476 | 12/1978 | Rock | 210/659 |
|---|---|---|---|
| 4,137,011 | 1/1979 | Rock | 417/22 |
| 4,233,156 | 11/1980 | Tsukada et al. | 73/61.1 C |
| 4,372,150 | 2/1983 | Stephens et al. | 73/61.1 C |
| 4,420,393 | 12/1983 | Smith | 210/198.2 |
| 4,450,574 | 5/1984 | Schwartz | 364/502 |
| 4,552,513 | 11/1985 | Miller et al. | 417/18 |
| 4,618,935 | 10/1986 | Schwartz | 364/510 |
| 4,629,561 | 12/1986 | Shirato et al. | 73/61.1 C |
| 4,733,152 | 3/1988 | Allington | 210/101 |
| 4,772,388 | 9/1988 | Allington | 73/61.1 C |
| 4,775,481 | 10/1988 | Allington | 210/198.2 |
| 4,781,824 | 11/1988 | Allington | 210/101 |

OTHER PUBLICATIONS

Spectra Physics SP8700 Pump Sofare.
Spectra Physics SP8700 Solvent Delivery System, 12 pages, published for Spectra—Physics.

Primary Examiner—Parshotam S. Lall
Assistant Examiner—Christopher L. Makay
Attorney, Agent, or Firm—Skjerven, Morrill, MacPherson, Franklin & Friel

[57] ABSTRACT

There is disclosed herein a system for testing the flow stability of the pumping system for liquid chromatography. The system determines the flow rate and determines the number of revolutions over which the flow rate is to be measured from the flow rate. The system then measures the value of a signal which is related to the flow rate multiple times for each revolution. The maximum value and the minimum value for each revolution is recorded. After the data from the requisite number of revolutions is collected, a calculation is performed which determines the flow stability indicator which is displayed. The calculation takes a multiple of the difference between the maximum of maximums and the minimum of minimums and divides it by the sum of the maximum of maximums and the minimum of minimums.

19 Claims, 4 Drawing Sheets

FLOW STABILITY REPORTING SYSTEM FOR A LIQUID CHROMATOGRAPHY SYSTEM

BACKGROUND OF THE INVENTION

The invention pertains to the field of liquid chromatography systems (hereafter LC), and, more particularly, to the field of flow stability measurement systems for LC systems.

In LC systems, the proper functioning of the system in identifying the components in a sample and their quantities depends upon a stable flow rate of solvent carrying the sample through the column. In the prior art, flow rate stability systems typically timed the time it took the pump shaft to travel through one revolution and compared the time for each cycle to a constant for the desired flow rate. Typically, such pumps are controlled by control systems which alter the motor speed to maintain a constant desired flow rate. If air bubbles or other problems caused the flow rate to change, this fact would be reflected in a change of the actual pressure of solvent at the head of the LC column. Because typical control systems monitor this pressure and compare it to a target pressure set by a computer to establish the desired flow rate, the changes in actual pressure resulted in non zero error signals which caused the motor speed to be changed to compensate in the direction needed to maintain the constant flow rate. These changes in pump speed would be reflected in the time per revolution. Thus problems like air leaks into the system which caused instability of flow rate could be detected by looking at revolution times.

The problem with these prior art systems is that they are slow to respond and difficult to interpret. Typically, such systems had 100 bits, one of which was assigned to each of the 100 most recent revolutions of the pump shaft. Each time a revolution time differed from a constant defining the time it should have taken at the pertinent flow rate, the bit for that revolution would be set. Typically, when the pump is first turned on, the first few cycles are all "bad" and these first bits would be remembered for the first 100 cycles even though the system is stable. At low flow rates, these first bad cycles would be part of the most recent 100 cycles for up to an hour. Thus, the user could misinterpret the report of say 5 bad cycles as a problem, when in fact the system has stable flow in the steady state. The correct way to interpret such systems was if the number of bad cycles was stable and not growing. Further, such systems usually had thresholds that would cause a report of a problem only if the number of bad cycles exceeded the threshold. Thus mediocre performance that did not exceed the threshold might not be detected if it was stable and not a growing number. Also, a major failure of stability on only one cycle would only be reported as one more bad cycle and no measure of the magnitude of the problem would be presented in the prior art systems.

Thus, there arose a need for a system which could give a faster response which was easier to interpret and which gave a quantitative measure of the magnitude of the flow stability problem.

SUMMARY OF THE INVENTION

According to the teachings of the invention, an apparatus is disclosed herein which functions to measure the flow stability in real time and report a number which is a measure of the magnitude of the flow stability problem if any. The system of the invention resides in the computer controlling the pump speed. The control system of the pump motor has an inner loop and an outer loop. The inner loop is responsive to the actual pressure at the head of the LC column and generates an actual pressure feedback signal to a difference amplifier that generates an error signal by comparing the actual pressure to a target pressure signal. The target pressure signal is calculated and generated by a computer in the outer loop. The purpose of the outer loop of the control system is to detect the actual shaft position of the pump and to measure the time of each revolution and calculate the shaft speed. The shaft speed is directly proportional to the flow rate through the column. The calculated shaft speed and flow rate are then compared to a desired flow rate which is determined from an external signal entered by a user or by another system. The actual flow rate is compared to the desired flow rate, and the target pressure signal is generated.

The flow stability measurement system according to the invention records the target pressure 4 times during each revolution of the pump shaft. The minimum and maximum target pressure from each revolution is recorded in a pair of memory locations. After this process has been repeated for 10 cycles, a calculation is made wherein 2000 times the quantity equal to the maximum of all maximums minus the minimum of all minimums is divided by the sum of the maximum of maximums and the minimum of all minimums. The result of this calculation is an indication of the flow stability, and the magnitude of the flow stability problem if any.

The system also uses a variable number of cycles depending upon the flow rate. For flow rates below a predetermined minimum, only 5 revolutions are used. For flow rates above a predetermined level, 40 revolutions are used.

DETAILED DESCRIPTION OF THE PREFERRED EMBODIMENT

Figure 1:
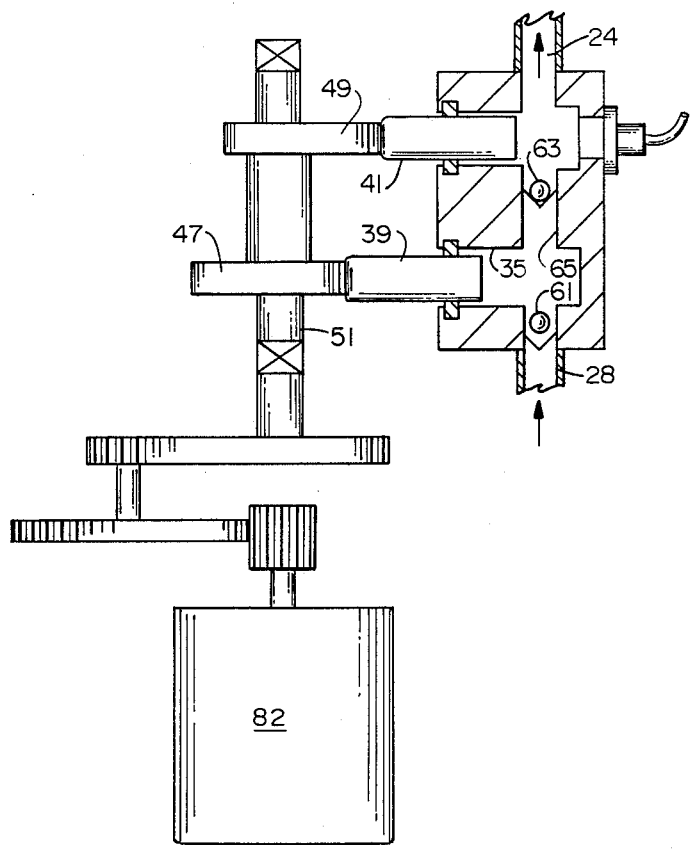
FIG. 1 is a diagram of a typical pump with check valves which can be monitored by the invention.

Referring to FIG. 1, there is shown a diagram of a typical pump used in LC systems to pump solvent into the column carrying the sample to be analyzed. The pump has a solvent input 28, a solvent output 24 connected to the LC column and two pistons 39 and 41. The pistons are driven by separate cams 47 and 49 so that their respective compression strokes are out of phase. An input check valve 61 allows only one way flow of solvent into the first cylinder 35 if it is working properly, and a second output check valve 63 allows only one way flow out of the pump outlet 24 under the influence of piston 41 during its compression stroke. The flow rate of solvent out from outlet 24 is set by the rotational speed of the cams 47 and 49 which are driven by the pump shaft 51.

Figure 2:
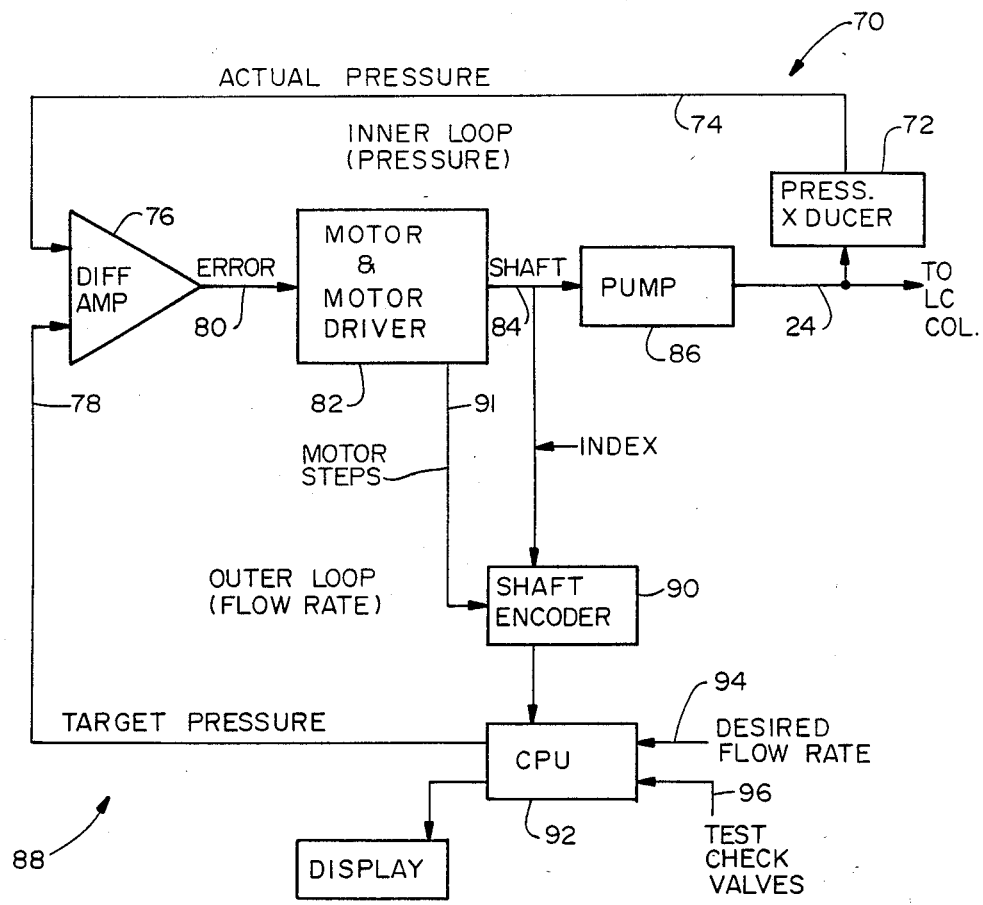
FIG. 2 is a diagram of the typical control loops used to control the pump of FIG. 1.

Referring to FIG. 2, there is shown a block diagram of the control system typically used with the pump of FIG. 1. The inner loop 70 senses the actual pressure on the outlet line 24 to the column via a pressure transducer 72 and uses the actual pressure signal from the transducer on line 74 as one input to a differential amplifier 76. The other input to this amplifier is the target pressure signal on line 78 from the outer loop. These two signals are compared to generate an error signal on line 80. The error signal is coupled to the motor driver and motor 82 and controls the motor speed. The motor drives a shaft 51 which drives the pump 86 such as is shown in FIG. 1. The outer loop 88 shown in FIG. 2 senses the shaft speed via a shaft encoder or other device 90. The shaft encoder generates a signal used by a computer 92 to determine the pump speed and therefore to determine the flow rate of solvent in the output line 24. The computer also receives a desired flow rate signal on line 94 and uses this signal to compare to the actual flow rate as indicated by the signal from the shaft encoder to set the target pressure signal on line 78 to correct the actual flow rate to be the desired flow rate. The shaft encoder also provides data regarding the absolute shaft position relative to an index point. This data provides the computer with real time information as to the actual position of each of the cams 47 and 49 and the status of the pistons 39 and 41 at each point in time. An index point is detected which defines a known position of the cams. The pump is driven by a stepper motor 82. The steps translate to known rotational positions of the shaft. The computer is coupled to the motor driver through the line 91 so that the steps can be counted and the shaft position at any point in time may be known.

Figure 3A:
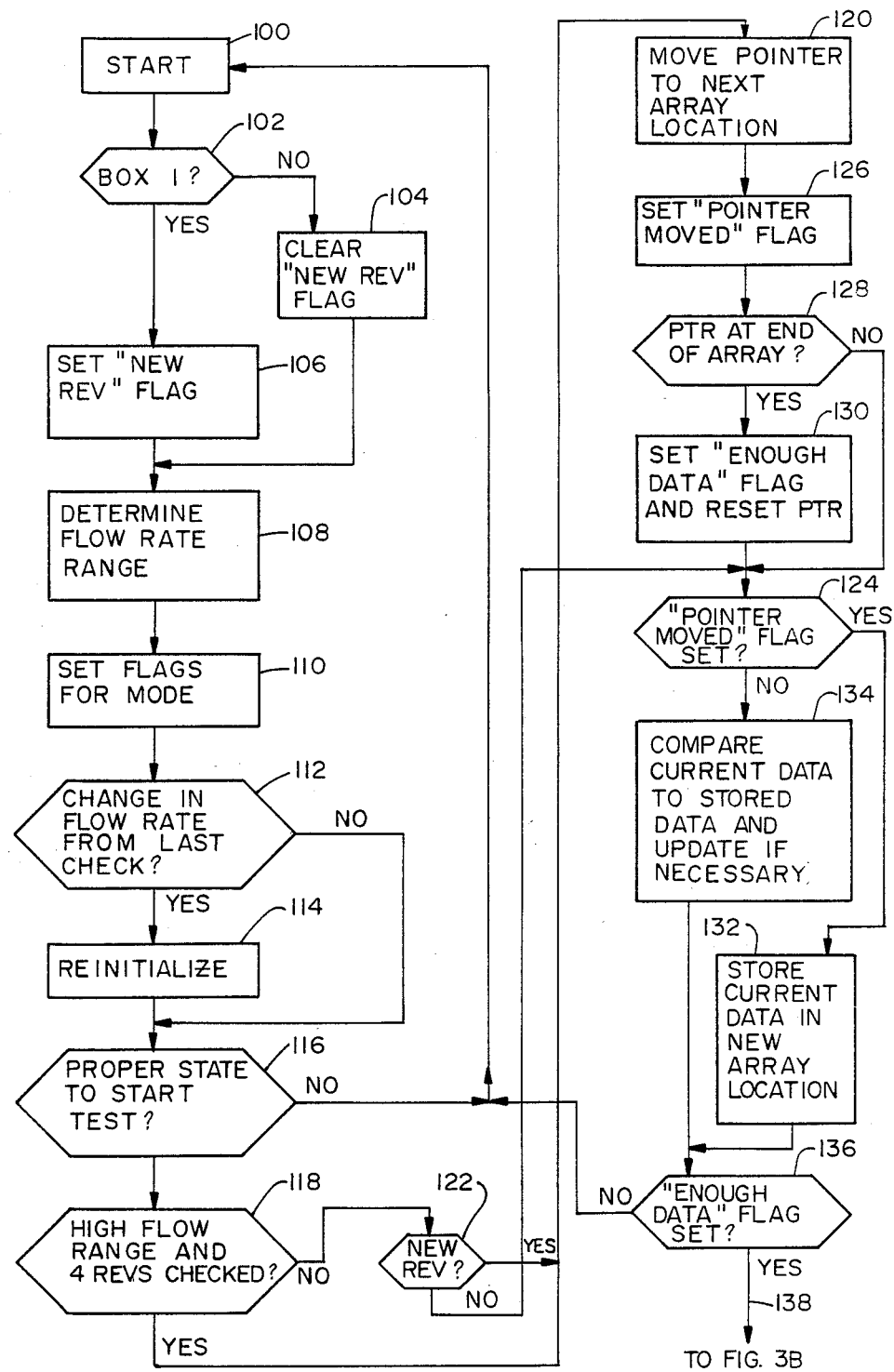
FIG. 3 is a flow chart of the program run in the computer in the invention to check the flow stability.
Figure 3B:
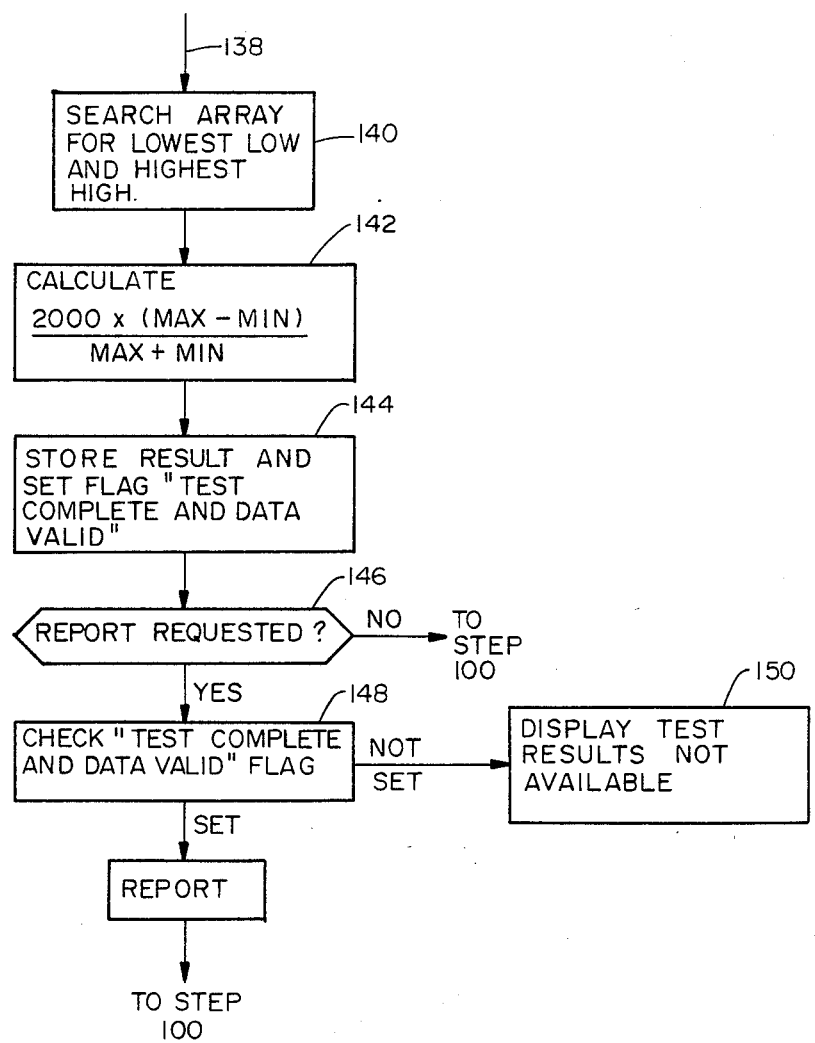

FIG. 3 is a flow chart of the program implemented by the computer 92 to perform the flow stability measurements according to the teachings of the invention. Block 100 represents test start. The test may be run periodically, continuously or only upon demand. Next, a test is performed to determine if the pump shaft is at the start of box 1. Each pump shaft revolution is divided into 5 "boxes" relating to different angular segments of one complete revolution of each cam. The invention contemplates timing less than a complete revolution and using different portions of the revolution depending upon whether the flow rate is low, medium or high. In the dual piston pump shown in FIG. 1, there is a double flow region wherein both pistons are in compression strokes. This happens during the 5th box, and the timing during this box can vary markedly depending upon certain factors including the compressibility of the solvent (at the high pressures used in LC systems, liquids are compressible). Because the timing of this box is not a reliable indication of flow rate, in the preferred embodiment, this box is not included in the timing for one "revolution". In alternative embodiments, some other portion of the revolution or the complete revolution may be used. Step 102 represents the step of determining whether the start of the portion of the revolution to be timed has been reached.

If the shaft position is not at the beginning of the portion the revolution to be timed, step 104 is performed to clear the new revolution flag. If the shaft is at the start of the portion to be timed, the step 106 is performed to set the new revolution flag. Next, a step 108 is performed to determine the flow rate range. This is done by looking at the current flow rate as computed by the routine that calculates the target pressure signal (not shown) and comparing this flow rate to a pair of constants that are arbitrarily set to determine a low, medium and high flow rate range. Next, a step 110 is performed which sets flags to indicate the mode. At low flow rates, only 5 revolutions are checked to provide faster response times. In the mid range of flow, 10 revolutions are checked. In the high flow rate range, 40 revolutions are checked. The flags set by step 110 determine the size of the buffer to be used to store the target pressures. The flags are checked by the steps that determine when to reset the array pointer to the first location in the array since the flag settings define how long the buffer, i.e., array, should be.

Next, a step 112 is performed to determine if there has been a change in flow rate from the last flow rate check. If there has been a change, step 114 is performed to reinitialize the system. This step represents the process of resetting an array pointer to the top of the array where the target pressures are stored, resetting the mode flags after finding the flow rate range encompassing the current flow rate, resetting the "enough data" flag, clearing the "new revolution" flag, and clearing the count of how many revolutions of data have been stored in the array.

After reinitialization, step 116 is performed to determine if the pump is in the proper state to collect data as part of the test. The first part of this test is to determine if the pump is referenced to the proper pump speed and under the flow control of the outer loop. If this is true, then a test is performed to determine if the first revolutions after start up have already been performed. These first revolutions after pump start are almost always unstable and do not provide valid data. To prevent bad data from these revolutions from being collected, an arbitrarily set number of these first revolutions are thrown out and no data is collected. If these two conditions are not met, processing returns to step 100.

If conditions are right to start the test, data is collected. This is done by sequentially filling a buffer with target pressure values. The buffer is organized as an array which has two storage locations for each revolution, one for storing the highest target pressure during each rotation and one for storing the lowest target pressure during the revolution. At low and medium flow rates, multiple target pressure readings are taken during each revolution. The lowest of these readings is stored in the low location and the highest of these readings is stored in the high location. At high flow rates, multiple readings during each of four revolutions are checked for each pair of storage locations. The lowest target pressure read during any of these four revolutions is stored in the low location and the highest target pressure is stored in the high location. The array is 5 pairs of storage locations long for low flow rates and 10 pairs of storage locations long for medium and high flow rates. Data is loaded into the array at the location of a pointer which is the address of the current array locations in use.

The data collection step starts with step 118. This step is a test for whether the high flow rate range encompasses the current flow rate and for whether 4 revolutions of data have been tested for loading at the current pointer location. If both of these conditions are satisfied, processing proceeds to step 120 where the pointer is incremented to the next array location. If both conditions are not satisfied, a step 122 is performed. This step tests the new revolution flag to determine if it is set. If it is, processing proceeds to step 120. If the new revolution flag is not set, processing proceeds to step 124 to be explained below.

Step 126 is performed after step 120 to set the "pointer moved" flag. Then, step 128 is performed to determine if the pointer has moved past the end of the array. If it has, step 130 is performed to set the "enough data" flag and to reset the pointer location to the beginning of the array. Next, the step 124 is performed to test whether the "pointer moved" flag has been set. If it has, step 132 is performed where the current target pressure is stored in both the low and high registers of the current array location. Step 132 also represents a resetting of the "pointer moved" flag. Since this step is reached only after the pointer has been reset to the top of the array, this step represents an overwriting of whatever are the contents at the beginning of the array. If the "pointer moved" flag has not been set, step 134 is performed. This step compares the current target pressure data with the stored data in the array locations at the current pointer position. If the current data is lower than the value of the memory location storing the lowest value recorded to date, the contents of that memory location are overwritten with the current value. If the current data is higher than the contents of the memory location storing the highest value recorded to date, the contents of that memory location are overwritten with the current value.

Thereafter, step 136 is performed to test whether the "enough data" flag is set. If it is not set, processing returns to step 100 because the array has not yet been filled. If it has been set, the array is full, and calculation of the flow stability value can be performed. Processing is then directed to step 140 via path 138 to begin the calculation.

Step 140 symbolizes the process of searching the array for the lowest low and the highest high of the stored target pressures. Although it may not be intuitively obvious, the target pressures are directly proportional to the flow rate since the target pressure will be matched by the actual pressure by the action of the inner control loop in causing the error signal to be non zero when the target pressure and the actual pressure are not the same. This non zero error signal alters the motor speed until the actual pressure approaches the target pressure as closely as possible. The actual pressure at the head of the LC column is directly proportional to the flow rate through the column. Thus, the target pressures are a good indication of the flow rate through the column. In alternative embodiments, the flow rate may be measured directly, the pump shaft speed may be measured, the actual pressures may be recorded or any other indicator of the flow rate may be recorded over several cycles to obtain the desired indicator of the stability of the flow rate.

Step 140 passes the value of the lowest low and the highest high values of target pressure from the array to step 142 where the flow stability indicator is calculated. The formula used for this calculation is as shown inside the box representing step 142. The max and min variables in the formula are the values passed from step 140. In some embodiments a transducer zero error factor may be added to the formula.

Next, step 144 is performed to store the result of the calculation and set a flag "test complete and data valid". Step 146 is then performed to test whether the user has indicated that a report of the flow stability indicator has been requested. If not, processing returns to step 100. If a report has been requested, step 148 is performed to check the "test complete and data valid" flag. If it is not set, step 150 is performed to display a message that the test results are not available yet. If the flag is set, step 152 is performed to display the result.

Although the invention has been described in terms of the preferred and various alternative embodiments disclosed herein, those skilled in the art will appreciate other alternative embodiments which do not depart from the true spirit and scope of the invention. All such embodiments are intended to be included within the scope of the claims appended hereto.

What is claimed is:

1. An apparatus for testing the flow stability in a column of liquid in a liquid chromatography system comprising:

means for pumping liquid through the column of said liquid chromatography system including a pump motor controlled by a control system that generates a control signal to control the flow rate based upon input data;

means for measuring the value of said control signal a plurality of times over a plurality of cycles and for recording the lowest value of said control signal for each revolution and the highest value of said control signal for each revolution and for calculating a flow stability criterion using the following formula:

$$\text{flow stability criterion} = \frac{2000 \times (\max - \min)}{\max + \min}$$

where, max = the maximum of maximum value for said control signals over all the recorded values for all the revolutions tested, and min = the minimum of the minimum values for said control signals over all the recorded values for all the revolutions tested.

2. The apparatus of claim 1 further comprising means for checking the flow rate and for recording the values for said control signal over a number of revolutions determined from said flow rate.

3. The apparatus of claim 2 wherein the means for measuring said control signal measures the value of said control signal 4 times during each revolution.

4. The apparatus of claim 3 wherein the means for measuring said control signal measures the maximum and minimum values for said control signal during each revolution for each of at least 10 revolutions.

5. The apparatus of claim 1 further comprising means in said means for measuring for altering the number of revolutions during which said measurements of minimum and maximum magnitudes of said control signal are made prior to calculating said flow stability criterion such that fewer revolutions are used for low flow rates and more revolutions are used for higher flow rates.

6. The apparatus of claim 5 wherein said means for altering the number of revolutions alters the number of revolutions to 5 for low flow rates and alters the number of revolutions to 40 for high flow rates.

7. An apparatus for testing the flow stability in a column of liquid in a liquid chromatography system comprising:

means for pumping liquid through the column of said liquid chromatography system using a pump controlled by a control system that generates a control signal in the form of a target pressure which is compared to the actual pressure at said column for purposes of controlling the shaft speed of said pump to obtain a desired flow rate wherein said target pressure is updated one or more times during each revolution;

means for storing the maximum value and minimum value of said target pressure a plurality of times during each revolution for each of a plurality of revolutions, where the number of revolutions during which the maximum and minimum values are recorded is varied according to the flow rate, where the stored maximum and minimum values represent a measure of a degree of variations of the flow rates of the liquid; and means for calculating a flow stability criterion using the following formula:

$$\text{flow stability criterion} = \frac{2000 \times (\text{max} - \text{min})}{\text{max} + \text{min}}$$

wherein:

max=the maximum of maximum values for said target pressure over all the revolutions for which maximum values were measured since the last calculation of said flow stability criterion;

min=the minimum of the minimum values for said target pressure over all the revolutions for which minimum values were measured since the last calculation of said flow stability criterion.

8. The apparatus of claim 7 further comprising means for providing programmability for when said flow stability criterion testing is done such that testing may be done not at all, continuously or only upon demand.

9. The apparatus of claim 8 further comprising means for determining when the pump shaft is in a portion of the revolution wherein measurements of said target pressure are a reliable indication of flow rate before making any measurements of maximum and minimum target pressures during any particular revolution.

10. The apparatus of claim 9 further comprising means for determining a low, medium and high flow rate range and for setting the number of revolutions for recording target pressures prior to each flow stability criterion calculation based upon said flow rate range.

11. The apparatus of claim 10 further comprising means for determining if a flow rate change has occurred since the last calculation of flow rate stability and for reinitializing the means for calculating so that all new maximum target pressure values and minimum target pressure values are collected for the number of revolutions appropriate for the new flow rate prior to calculation of said flow stability criterion.

12. The apparatus of claim 11 further comprising means for determining if a predetermined number of initial revolutions of said pump have occurred prior to beginning the process of collecting said maximum and minimum target pressure values to insure high reliability in said flow stability criterion.

13. The apparatus of claim 12 further comprising buffer means for storing said maximum and minimum target pressure values, wherein therein are two storage locations designated for each revolution and wherein said measuring means measures said target pressure a plurality of times during each revolution and stores the lowest value for the current revolution in one of said locations corresponding to the current revolution and stores the highest value for the current revolution in the other of said location corresponding to the current revolution and further comprising pointer means for identifying the current pair of storage locations corresponding to the current revolution.

14. The apparatus of claim 13 further comprising means for displaying a message regarding the status of the calculation during times when data is still being collected and to display the results when the requisite data has been collected and the calculation has been made.

15. A method of measuring flow stability in a liquid chromatography system having a pump and a column comprising the steps of:

controlling the shaft speed of said pump using a target pressure at the column compared to the actual pressure at the column to control the flow rate by controlling the pump speed;

measuring the maximum value of said target pressure and the minimum value for said target pressure during each revolution for a plurality of revolutions at the same flow rate;

recording said maximum and minimum values;

calculating a flow stability criterion using the following relationship:

$$\frac{2000 \times (\text{max} - \text{min})}{(\text{max} + \text{min})} = \text{flow stability criterion}$$

where, max=the maximum of the maximum values for said control signals over all the recorded values for all the revolutions tested, and min=the minimum of the minimum values for said control signals over all the recorded values for all the revolutions tested.

16. The method of claim 15 further comprising the step of determining the flow rate range and setting the number of revolutions for which said maximum and minimum target pressures are measured based upon said flow rate.

17. The method of claim 16 further comprising the step of determining whether a predetermined number of initial revolutions have been completed prior to beginning the process of collection of target pressure values.

18. The method of claim 17 further comprising the step of checking to determine if the flow rate has changed since the last calculation of the flow rate stability criterion or during the collection of data for the present flow rate stability criterion calculation and eliminating any target pressure data collected at flow rates other than the current flow rate.

19. The method of claim 18 further comprising the step of displaying a message regarding the status of the flow rate stability criterion calculation during collection of the data and for displaying the flow rate stability criterion calculation result when the calculation is completed.

* * * * *

UNITED STATES PATENT AND TRADEMARK OFFICE
CERTIFICATE OF CORRECTION

PATENT NO. : 4,905,161

DATED : 02/27/90

INVENTOR(S) : Miller, et al.

It is certified that error appears in the above-identified patent and that said Letters Patent is hereby corrected as shown below:

IN THE CLAIMS:

Column 6, line 27, Claim 1, "value" should read --values--

Column 6, line 36, Claim 2, "for" should read --of--

Column 7, line 16, Claim 7, "wherein" should read --where--

Column 7, line 52, Claim 12, "high" should read --higher--

Signed and Sealed this

Third Day of September, 1991

*Attest:*

HARRY F. MANBECK, JR.

*Attesting Officer*     *Commissioner of Patents and Trademarks*